United States Patent [19]

Noetzel et al.

[11] 3,991,010
[45] Nov. 9, 1976

[54] PROCESS FOR PREPARING FLAME RESISTANT PLASTICS MATERIALS

[75] Inventors: Siegfried Noetzel, Kelkheim, Taunus; Horst Jastrow, Niederhochstadt, Taunus; Edgar Fischer, Frankfurt am Main, all of Germany

[73] Assignee: Hoechst Aktiengesellschaft, Frankfurt am Main, Germany

[22] Filed: Jan. 16, 1975

[21] Appl. No.: 541,562

[30] Foreign Application Priority Data

Jan. 18, 1974 Germany............................ 2402268

[52] U.S. Cl....................... 260/45.7 P; 260/2.5 FP; 260/880 R; 260/961
[51] Int. Cl.²............................................ C08K 5/53
[58] Field of Search ............ 260/45.7 P, 961, 880 R

[56] References Cited
UNITED STATES PATENTS

| | | | |
|---|---|---|---|
| 3,046,236 | 7/1962 | Jahn.................................... | 260/2.5 |
| 3,223,755 | 12/1965 | Rimmer.............................. | 260/986 |
| 3,250,827 | 5/1966 | Schroll............................... | 260/961 |
| 3,325,563 | 6/1967 | Taylor et al. ....................... | 260/921 |
| 3,803,271 | 4/1974 | Chiddix et al. ..................... | 260/956 |
| 3,830,886 | 8/1974 | Davis et al. ........................ | 260/953 |
| 3,830,890 | 8/1974 | Kerst et al. ........................ | 260/932 |
| 3,842,048 | 10/1974 | Jin ..................................... | 260/78.5 |
| 3,886,237 | 5/1975 | D'Alelio............................. | 260/956 |

OTHER PUBLICATIONS

Gefter, "Organophosphorus Monomers and polymers", 1962, p. 12.
Kosolapoff, "Organophosphorus Compounds,"1950, pp. 139, 140 and 155.

*Primary Examiner*—Lewis T. Jacobs
*Assistant Examiner*—R. A. White
*Attorney, Agent, or Firm*—Curtis, Morris & Safford, P.C.

[57] ABSTRACT

The present invention relates to 1,2-dibromoethane phosphonic acid bis-(2,3-dibromopropyl) ester, to a method for preparing the same, and to moldable plastics materials with improved flame retarding characteristics containing 1,2-dibromoethane phosphonic acid bis-(2,3-dibromopropyl) ester as the flame proofing agent.

9 Claims, No Drawings

PROCESS FOR PREPARING FLAME RESISTANT PLASTICS MATERIALS

It is known that easily inflammable plastics materials may be rendered flame resistant by adding halogen compounds. Flame proof mixtures of plastics materials are especially important for preparing porous thermoplastic materials, especially foam plastics of styrene polymers.

Examples of suitable well-known agents for flameproofing plastics are highly chlorinated non-volatile hydrocarbon compounds. They are preferably used with antimony trioxide. This method has the disadvantage that relatively large quantities of the chlorinated hydrocarbons, generally from 15 to 20% by weight of the amount of the plastics material, must be used in order to obtain an adequate flame retarding effect. This is especially disadvantageous in the preparation of foamed plastics from expandable thermoplastics materials. The high content of halogen compounds adversely affects the fusion of the granular materials. Foamed plastics of low mechanical resistance are often obtained.

It is further known that organic bromine compounds are by far more efficient than the corresponding chlorine compounds. However not all bromine compounds can be used as flame retarding agents. Suitable flameproofing bromine compounds are for example, tetrabromobutane, dibromoethylbenzene, dibromopropanol, tris(2,3-dibromopropyl) phosphate, 2-bromoethylphosphonic acid bis-(2-bromoethyl)ester, tetrabromocyclooctane or hexabromocyclododecane. They are generally used in an amount of from 5 to 10% by weight calculated on the plastics material. A suitable agent for flame-proofing plastics materials must have the following characteristics above all: it must be difficultly volatile and odorless and must not adversely affect the mechanical properties of the plastics materials. It must be efficient in an amount as small as possible. It must not stimulate corrosion and it must be possible to add it to the monomer compounds prior to polymerization, without interference with the polymerization process. A necessary condition therefore is that the bromine compound is readily soluble in the monomer to be polymerized, for example in styrene.

The above mentioned requirements as applied to organic bromine compounds having a flame retarding action are rarely satisfied. Some of the compounds are volatile so that the treated plastics materials are no longer flame-proof after a period of time and some of the compounds have an unpleasant odor. One series of known bromine compounds has a plasticizing effect. Flame retarding agents having plasticizing properties are unsuitable for preparing foamed plastics from expandable granular thermoplastic materials owing to the fact that foamed plastics having an unsatisfactory pressure and volume stability are obtained. Finally most organic compounds interfere with the polymerization of polymerizable monomers.

Consequently they cannot be mixed with the monomers, but only with the ready-made plastics materials. The solubility of the flame-retarding agent in the polymerizable monomer, for example styrene, is often so low that addition in the course of the polymerization is impossible. It is true that one series of flame-retarding agents is soluble in the monomer to be polymerized, but they completely crystallize owing to their incompatibility with the polymer, thus reducing the flame-retarding effect.

The compound 1,2-dibromoethanephosphonic acid bis-(2,3-dibromopropyl)ester of the formula

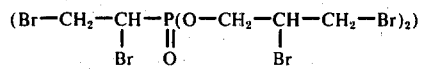

has now been found.

It has also been found that flame resistant moldable thermoplastic materials are obtained by adding thereto as a bromine containing organic phosphorus compound from 0.3 to 6% by weight of 1,2-dibromoethanephosphonic acid bis-(2,3-dibromopropyl)ester.

The phosphonic acid ester according to the invention is prepared by known methods. One method consists in reacting 1 mole of vinyl phosphonic acid dichloride in an inert solvent such as chloroform with 2 moles of allyl alcohol in the presence of 2 moles of triethylamine. The vinylphosphonic acid diallyl ester obtained in a good yield absorbs 6 equivalents of bromium at room temperature within about 5 hours, 1,2-dibromoethanephosphonic acid bis-(2,3-dibromopropyl)ester being obtained.

The flame retarding phosphonic acid ester according to the invention is odorless. It has practically no vapor pressure and consequently does not volatilize. Flame resistant mixtures containing the aforesaid flame retarding agent do not lose their flame resistance even after storage for a long time.

Compared to the brominated phosphoric acid esters described in German Patent Specification No. 1,046,313 the phosphonic acid ester according to the invention has a substantially better hydrolysis stability.

The compound according to the invention is compatible with a series of plastics such as polystyrene. All easily inflammable plastics such as polymers and copolymers of ethylene, propylene, acrylonitrile, acrylic acid ester, methacrylic acid ester and vinyl acetate or thermo-setting resins such as unsaturated polyester resins and polyaddition compounds such as polyurethanes may be flame-proofed with the compound according to the invention. Said compound is especially suitable for flame-proofing styrene polymers such as polystyrene and copolymers of styrene and acrylonitrile and/or butadiene-1,3.

The phosphonic acid ester according to the invention has the further advantage that it does not affect the shrinking properties of foamed plastics blocks for example of polystyrene. Compared to the brominated phosphonic acid esters of the formula

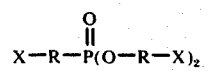

known for example from German Offenlegungsschrift No. 1,495,419 and to the brominated butadiene polymers, the phosphonic acid ester according to the invention has the advantage that it can be added to the plastics material in a smaller quantity and still give the same degree of flame-resistance is obtained.

The flame-proof mixtures may be prepared in different ways. Homogeneous mixtures of plastics and the flame-retarding agent according to the invention may be prepared, for example, by mixing the plastics materials and the bromine containing phosphonic acid ester at a temperature below 170° C in an extruder or kneader. Both components may also be dissolved in one solvent, which solvent is subsequently removed. The mixture may also be obtained advantageously by polymerizing monomer compounds in the presence of the flame-retarding compound and optionally of peroxides such as ditertiary butyl peroxide which decompose at higher temperatures and act as synergistic auxiliaries. The latter method is especially important for preparing beads of flame resistant expandable styrene polymers by polymerizing styrene with easily volatile aliphatic hydrocarbons or their fluorine and/or chlorine derivatives, which polymerization is advantageously carried out in aqueous suspension. In other methods the preparation of intimate mixtures is dispensed with. In the case of plastics materials in the form of granular beads the surfaces of the granules are coated. This method is important in the case of expandable granular materials, especially in the case of beads of expandable styrene polymers containing as foaming agents easily volatile aliphatic hydrocarbons or their halogen derivatives.

The following examples illustrate some of the methods for preparing flame resistant mixtures.

The addition of peroxides is also advantageous if the bromine compound is added to the ready made polymer. Peroxides having a half-life of at least 2 hours at 100° C (determined in benzene) are preferably used. Examples of suitable peroxides are: dicumyl peroxide, tertiary butyl hydroperoxide, di-tertiary butyl peroxide, pinanehydroperoxide and cumyl hydroperoxide.

Mixtures of two or more peroxides may also be used.

EXAMPLE 1

Preparation of 1,2-dibromoethanephosphonic acid bis-(2,3-dibromopropyl)ester a. Preparation of vinylphosphonic acid diallyl ester 146 g of vinylphosphonic acid dichloride (1 mole) were added while stirring to a solution of 116 g (2 moles) of allyl alcohol in 1000 ml of anhydrous chloroform at 0° C and subsequently 288 g of triethylamine were introduced dropwise within approximately one hour. After suction, the solid residue (triethylamine hydrochloride) was dissolved in water, the oily layer formed was separated and combined with the filtrate. The filtrate was extracted four times with 600 ml of water each time in order to remove the chlorine, dried over sodium sulfate and the chloroform was distilled off in the rotation evaporator. 190 g of a brown liquid were obtained, having a boiling point of from 75° to 80° C at 5 mm Hg.

b. Bromination of vinylphosphonic acid diallyl ester 188 g of vinylphosphonic acid diallyl ester were dissolved in 300 ml of chloroform and a solution of 480 g of bromine in 350 ml of chloroform was introduced dropwise within half an hour. Two thirds of the bromine solution was instantly decolored while being introduced. The reaction mixture was stored over night at 25° C and boiled while adding active carbon. After filtering off the active carbon and distilling off the chloroform a clear, viscous oil was obtained.

molecular weight: 668, corresponding to the theoretical formula $C_8H_{13}O_3PBr_6$ analysis: calculated: 14.4% of C; 2.0% of H; 4.6% of P; 71.7% of Br; found: 14.6% of C; 2.0% of H; 4.7% of P; 71.1% of Br

EXAMPLE 2 (and the following examples)

Flame-proofing of plastics materials with 1,2-dibromoethanephosphonic acid bis-(2,3-dibromopropyl)ester a. Comparative example according to the state of the art:

A 20% solution of polystyrene (RSV (reduced specific viscosity) = 1.4 dl/g, determined in a solution of 1 g of polystyrene in 100 ml of benzene at 25° C) in methylene chloride was prepared. 100 g of the solution obtained were mixed while stirring with 0.53 g of 1,2,5,6,9,10-hexabromocyclododecane corresponding to 0.4% by weight of bromine and 0.5 g of di-tertiary butyl peroxide, the mixture was poured into an aluminium foil of 19 × 8 × 2 cm forming a dish and stored in a hood for 12 hours. After smoothing the aluminium foil, the polystyrene plate was covered by a further aluminium foil, the whole was placed into a perforated steel mold and dipped for 20 minutes into boiling water. The foamed foil was dried for 12 hours at 70° C and under pressure of 400 mm under a nitrogen atmosphere.

After flaming for 5 seconds with a nonluminous Bunsen flame in the way described in example 2b and after subsequently removing the flame the foil burnt away with an intensely soot-forming flame.

b. Example according to the invention:

A 20% solution of polystyrene (RSV = 1.4 dl/g, measured in a solution of 1 g of polystyrene in 100 ml of benzene at 25° C) in methylene chloride was prepared. 100 g of the solution obtained were mixed while stirring with 0.55 g of 1,2-dibromoethanephosphonic acid bis-(2,3-dibromopropyl)ester corresponding to 0.4% by weight of bromine and 0.5 g of ditertiary butyl peroxide, poured into an aluminium foil forming a dish (19 × 8 × 2 cm) and stored in a hood for 12 hours. The rest of the example was carried out as example 2 a). The flame-resistance of the foamed foil was tested as follows:

The foil was adjusted such that the shorter side formed an angle of 45° with regard to the horizontal line. The lower situated longitudinal side was flamed subsequently at three different places with a nonluminous Bunsen flame for 5 seconds each time. The foil was then turned by 90° so that the longitudinal side which was previously above was now below and this longitudinal side was also flamed as described. After each careful removal of the flame the burning foil was extinguished in all six cases within 1 to 2 seconds.

EXAMPLE 3

230 ml each of demineralized water and of styrene contained in a 1 liter glass flask, were heated to 90° C and a solution of 0.27% by weight of dibenzoyl peroxide, 0.12% by weight of t-butylperbenzoate, 2.2 g of 1,2-dibromoethane phosphonic acid bis-(2,3-dibromopropyl) ester and 0.5 g of di-tertiary peroxide in 45 ml of styrene were added thereto.

After polymerization of 54% by weight of the monomer styrene, a solution of 1.7 g of a commercially available polyvinyl alcohol (having a residual ester content of about 15%) in 100 ml of water was added, and a stable dispersion was obtained. The suspension polymerization was carried out for 10 hours at 90° C and for 3 hours at 115° C. After separating the aqueous phase the polymer beads were washed with water, isolated and dried for 12 hours at room temperature at the air. A 20% solution of the polymer in methylene chloride was prepared. A foamed foil was prepared from 100 g of the solution obtained as described in example 2 *a*) and flamed at six places in the way described in example 2 *b*). The extinguishing time after flaming was less than 1 second in all cases.

EXAMPLE 4

3.2 Parts by weight of 1,2-dibromoethanephosphonic acid bis-(2,3-dibromopropyl) ester and 0.5 part by weight of dibenzoyl peroxide were dissolved in a mixture of 70 parts by weight of styrene and 30 parts by weight of acrylonitrile. The solution was suspended in 200 parts by weight of water containing 0.8 g of barium sulfate as suspension stabilizer and polymerized for 20 hours at 70° C and for 10 hours at 80° C. The formed polymer particles were separated, washed and dried and sheets of a thickness of 1.3 mm were molded therefrom at 160° C. Test rods of 127 × 12.7 × 1.3 mm were cut from the sheets obtained. The horizontally fixed test rods were flamed at the free end with a nonluminous Bunsen flame for 30 seconds. The flame was extinguished before reaching the first mark which was situated at a distance of 25 mm from the free end. According to the burning test ASTM D 635–68 the product can be considered as non-burning.

EXAMPLE 5

A 20% solution of polystyrene (RSV = 1.4 dl/g, determined in a solution of 1 g of polystyrene in 100 ml of benzene at 25° C) in methylene chloride was prepared. 100 g of said solution were mixed while stirring with 0.2 g of 1,2-dibromoethanephosphonic acid bis-(2,3-dibromopropyl) ester and 0.05 g of di-tertiary butylperoxide the obtained mixture was poured into an aluminium foil forming a dish (19 × 8 × 2 cm) and stored for 12 hours in a hood. Thereafter the aluminium foil was smoothed, the polystyrene plate was covered with a further aluminium foil and the whole was placed in a perforated steel mold and dipped into boiling water for 20 minutes. The foamed foil was dried for 12 hours at 70° C under a pressure of 400 mm in a nitrogen atmosphere. The foamed foil was flamed at 6 places in the way described in example 2 *b*). The extinguishing time after flaming was less than 1 second in all cases.

What is claimed is:
1. In a flame resistant moldable plastics material essentially consisting of a thermoplastic material and from 0.3 to 6% by weight calculated on the quantity of the plastics material of a bromine containing organic phosphonic acid compound as flame retarding agent, the improvement which comprises using a flame retarding agent 1,2-dibromoethanephosphonic acid bis-(2,3-dibromopropyl) ester.
2. Flame resistant moldable plastics material as claimed in claim 1, containing besides the flame retarding agent at least one organic peroxide as synergist.
3. Flame resistant moldable plastics material as claimed in claim 1, containing besides the flame retarding agent at least one organic peroxide having a half life (in benzene) of at least 2 hours at 100° C as synergist.
4. Flame resistant moldable plastics material as claimed in claim 1, containing besides the flame retarding agent at least one organic peroxide from the group consisting of dicumylperoxide, tertiary butylhydroperoxide, di-tertiary butylperoxide, pinane hydroperoxide or cumylhydroperoxide as synergist.
5. Process for preparing flame resistant thermoplastic materials by introducing into the plastics material from 0.3 to 6% by weight calculated on the quantity of plastics material of a flame retarding agent or by polymerizing an unsaturated organic monomer or a mixture of such monomers in the presence of a flame retarding agent, said flame retarding agent being 1,2-dibromoethanephosphonic acid bis(2,3-dibromopropyl) ester.
6. Process as claimed in claim 5, wherein at least one organic peroxide is used additionally as synergist.
7. Process as claimed in claim 5, wherein at least one organic peroxide having a half life in benzene of at least 2 hours at 100° C is used additionally as synergist.
8. Process as claimed in claim 5, wherein the plastics material used is polystyrene or a copolymer of styrene and acrylonitrile or/and butadiene-1,3 or wherein the monomer used is styrene or a mixture of styrene and acrylonitrile or/and butadiene-1,3.
9. 1,2-Dibromoethanephosphonic acid bis-(2,3-dibromopropyl) ester.

* * * * *